US006726626B1

(12) United States Patent
Hossack

(10) Patent No.: US 6,726,626 B1
(45) Date of Patent: Apr. 27, 2004

(54) ELECTRIC CIRCUIT FOR TUNING A CAPACTIVE ELECTROSTATIC TRANSDUCER

(75) Inventor: John A. Hossack, Charlottesville, VA (US)

(73) Assignee: Sensant Corporation, San Leandro, CA (US)

( * ) Notice: Subject to any disclaimer, the term of this patent is extended or adjusted under 35 U.S.C. 154(b) by 9 days.

(21) Appl. No.: 10/222,002

(22) Filed: Aug. 14, 2002

(51) Int. Cl.[7] .................................................. A61B 8/00
(52) U.S. Cl. .................................... 600/437; 331/116 R
(58) Field of Search ................................ 600/437, 443, 600/447, 459; 310/309, 317, 334, 318; 331/116 R, 163, 155, 179, 158, 18

(56) References Cited

U.S. PATENT DOCUMENTS 3,739,299 A * 6/1973 Adler ...................... 331/116 R
5,675,296 A * 10/1997 Tomikawa .................. 331/158
6,461,299 B1 * 10/2002 Hossack ..................... 600/437

* cited by examiner

*Primary Examiner*—Francis J. Jaworski
*Assistant Examiner*—Ruby Jain
(74) *Attorney, Agent, or Firm*—Pillsbury Winthrop LLP

(57) ABSTRACT

An electrostatic transducer circuit and method of tuning the same, in which a balancing inductance is inserted into the electrostatic transducer circuit is described. The electrostatic transducer circuit generally includes transmit circuitry, receive circuitry and a capacitive electrostatic transducer. The balancing inductance is tuned to counteract the negative reactance of the capacitive electrostatic transducer at a desired operating frequency during the transmit mode. The balancing inductance is inserted into the transmit circuitry and is then isolated from the remaining parts of the electrostatic transducer circuit. Isolation is achieved by switching the electrostatic transducer circuit between transmit and receive modes of operation. Further, a receive circuit balancing reactance can also be included. The method provides a balancing inductance that is used to counteract negative reactance of the capacitive electrostatic transducer at a desired operating frequency during transmit mode.

46 Claims, 4 Drawing Sheets

ELECTRIC CIRCUIT FOR TUNING A CAPACTIVE ELECTROSTATIC TRANSDUCER

FIELD OF THE INVENTION

The present invention relates to the field of electro-acoustic transducer circuits. More specifically, the present invention relates to the inductive tuning of capacitive electrostatic micro-fabricated electro-acoustic transducers.

BACKGROUND

An electro-acoustic transducer is an electronic device used to emit and receive sound waves. These transducers are used in medical imaging, non-destructive evaluation and other applications. Ultrasonic transducers are electro-acoustic transducers that operate at higher frequencies, typically at frequencies exceeding 20 kHz.

The most commonly used type of ultrasonic transducer is the piezoelectric transducer (PZT) made of ceramic materials. In recent years, a revolutionary, new technology has been developed with the potential of displacing conventional piezoelectric ceramic-based ultrasound transducers used for medical ultrasound imaging. These new transducers are made of fine micro-fabricated membranes suspended above Silicon-based substrates. These transducers operate in an electrostatic mode and electrically approximate a parallel-plate capacitor with finely spaced plates. These micro-fabricated transducers have considerable potential since the micro-fabrication process gives rise to low cost, highly complex structures—such as finely pitched 2D arrays of elements. Furthermore, since the micro-fabricated transducers are based on Silicon, it is envisioned that suitable driver and receiver circuitry may be integrated onto the same Silicon substrate or onto one immediately adjacent to the transducer substrate. Thus, the micro-fabrication technology may enable 2D arrays and real-time 3D imaging, which until now has been hampered by the cost and complexity of the cumbersome, time consuming, low-yield manufacturing processes required for the ceramic-based arrays. The micro-fabrication technology may also enable new intravascular applications such as placing transducer arrays on the tips of catheters or on other temporary, or semi-permanent, minimally invasive monitoring instrumentation used inside the body to monitor physiological functions (e.g., blood flow, blood pressure, etc.).

One drawback of the electrostatic micro-fabricated transducer arrays is that they substantially behave with the electrical characteristics of a capacitor. The capacitance of the micro-fabricated transducer introduces a negative reactance component to the overall transducer impedance, which makes the transducer inefficient. What is needed is a way to tune out the negative reactance of the micro-fabricated transducer using inductive tuning, thereby making the transducer circuit more efficient. However, inductive tuning alone results in narrowband operation, which is also undesirable, because the narrowband operation prevents the transducer circuit from performing efficiently for harmonic imaging, which requires a broader operating bandwidth.

Harmonic imaging (i.e., filtering receive signal to around the second harmonic of the transmitted signal) has recently become the default imaging mode in medical diagnostic ultrasound. It has been found that by imaging the nonlinearly generated harmonic signal, one gets a far superior image in terms of both spatial and contrast resolution. Harmonic imaging applies to both imaging of tissue alone or imaging of introduced contrast agents. Harmonic imaging requires a moderate to high sound intensity since it is based on a nonlinear effect. Additionally, harmonic imaging inherently requires high transducer bandwidth or, alternatively, the ability to switch the frequency of high sensitivity between transmit and receive. Ultimately what is needed, is a solution to the problem for operating an inductively tuned, capacitance-based micro-fabricated transducer efficiently for harmonic imaging.

SUMMARY

It is an advantage of the present invention to provide a method for tuning out the negative reactance of a capacitive micro-fabricated electrostatic transducer, such as by using inductive tuning, thereby making the transducer circuit more efficient.

It is a further advantage of the present invention to provide a method for inductively tuning a capacitive micro-fabricated electrostatic transducer efficiently for harmonic imaging.

Still further, it is an advantage of the present invention to provide a capacitive micro-fabricated electrostatic transducer circuit with the negative reactance tuned out using inductive tuning, thereby making the transducer circuit more efficient.

It is a further advantage of the present invention to provide a capacitive micro-fabricated electrostatic transducer circuit, inductively tuned for efficient use in harmonic imaging.

The present invention achieves the above advantages, among others, singly or in combination, by providing an electrostatic transducer circuit in which a balancing inductance is inserted into an electrostatic transducer circuit. The electrostatic transducer circuit generally includes transmit circuitry, receive circuitry and a capacitive electrostatic transducer. The balancing inductance is tuned to counteract the negative reactance of the capacitive electrostatic transducer at a desired operating frequency during the transmit mode. The balancing inductance is inserted into the transmit circuitry and is then isolated from the remaining parts of the electrostatic transducer circuit. Isolation is achieved by switching the electrostatic transducer circuit between transmit and receive modes of operation. Further, a receive circuit balancing reactance can also be included.

In addition, the present invention achieves the above advantages, among others, singly or in combination, by providing a method of for tuning out the negative reactance of a capacitive micro-fabricated electrostatic transducer. The method provides a balancing inductance that is used to counteract negative reactance of the capacitive electrostatic transducer at a desired operating frequency during transmit mode.

BRIEF DESCRIPTION OF THE DRAWINGS

The above-mentioned and other features and advantages of the present invention will become more apparent from the detailed description set forth below when taken in conjunction with the drawings in which like reference characters identify correspondingly throughout and wherein.

DETAILED DESCRIPTION OF THE PREFERRED EMBODIMENT

Figure 1:
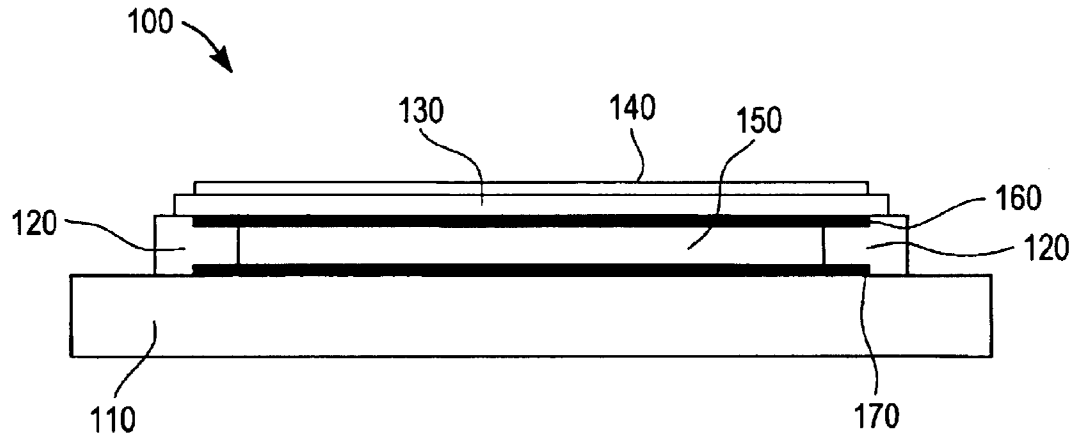
FIG. 1 (PRIOR ART)
FIG. 1 illustrates a conventional capacitive micro-fabricated electrostatic transducer.

According to one aspect of the present invention, a presently preferred embodiment inserts a tuned balancing reactance into the transmit side of an electro-acoustic transducer circuit. The electro-acoustic transducer circuit of the present invention includes a capacitive electrostatic transducer. The presently preferred embodiment tunes the balancing reactance to counteract the negative reactance of the capacitive electrostatic transducer at the desired operating frequency. The tuned balancing reactance of the present invention preferably uses an inductor. This balancing reactance may comprise a single series connected inductor. However, it may comprise additional components (e.g., additional inductor(s), transformer(s), etc.). This component (or these components) may be connected in series or in parallel or in combinations of series and parallel with respect to the capacitive transducer. The inductance in this preferred embodiment may include a real resistive characteristic in addition to the pure imaginary reactance presented by a perfect inductor. This resistive characteristic may be included by design (possibly by a series or parallel resistor) or as a result of the imperfections that are found in practical inductors. Additionally, the presently preferred embodiment isolates the balancing reactance from the receive circuit of the electro-acoustic transducer circuit. The isolation of the present invention includes switching between the transmit and receive circuits of the electro-acoustic transducer circuit using a switch. The present invention provides an improvement in sensitivity that assists in making the transducer performance more closely match, and possibly exceed, the performance of more conventional transducers used for these applications, such as PZT ceramic transducers.

The present invention is preferably used in the context of a high frequency, high channel count imaging array used for diagnostic imaging. The medium into which the capacitive electrostatic transducer is operated is typically tissue, which has an acoustic property that approximates water. Accordingly, the acoustic impedance of the acoustic membrane, described further herein, is very low compared to the impedance of the fluid. Thus, the capacitive electrostatic transducer circuit according to the present invention is substantially non-resonant when operated in tissue. And, since it is effectively non-resonant, it will have a large bandwidth. However, the electrical impedance near the frequency of interest includes a real part that may be on the order of 50–100 ohms, and a negative reactance, due to the capacitance of the transducer, on the order of several hundred to thousands of ohms. This high imaginary impedance restricts current flow into the capacitive electrostatic transducer.

The present invention will now be described in detail with reference to the accompanying drawings, which are provided as illustrative examples of preferred embodiments of the present invention.

FIG. 1 illustrates a conventional capacitive micro-fabricated electrostatic transducer 100. The capacitive micro-fabricated electrostatic transducer 100 includes a substrate 110 that contains a lower conductive plate 170 formed on a top surface of the substrate 110. Insulating supports 120, formed from, for example, silicon dioxide, are formed over the lower conductive plate 170. The insulating supports 120 are spaced at peripheral locations around the perimeter of membrane 130 so as to cause the membrane 130 to be in tension above a separation 150. The membrane 130 further contains a conductive portion that forms an upper conductive plate 160. This results in the separation 150 being located between the lower conductive plate 170 and the upper conductive plate 160. Additionally, the membrane 130 contains at least one signal electrode 140, which is also electrically connected to the upper conductive plate 160. As is known, the separation 150 is typically obtained using a sacrificial layer that is applied and subsequently removed after formation of other layers thereover, although other techniques can be used. And it is understood that this capacitive micro-fabricated electrostatic transducer is described for background purposes, and that other types of capacitive micro-fabricated electrostatic transducers fall within the scope of the present invention, as will be apparent from the further teachings and descriptions provided hereinafter.

The present embodiment operates, however, within the context of a capacitive micro-fabricated electrostatic transducer, and, as such, the capacitive micro-fabricated electrostatic transducer illustrated in FIG. 1 will be used to describe the present invention.

Figure 2A:
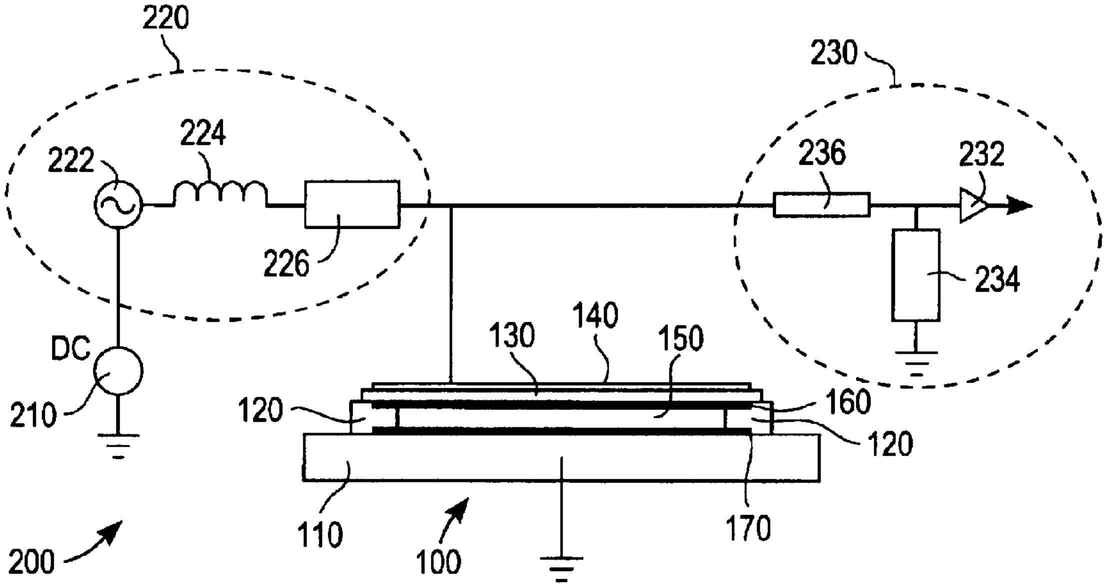
FIGS. 2A–2C illustrate a micro-fabricated capacitive electrostatic transducer with a switched balancing reactance according to an embodiment of the present invention.

FIG. 2A illustrates a presently preferred embodiment of the present invention; a capacitive, micro-fabricated electrostatic transducer circuit 200, which includes a capacitive micro-fabricated electrostatic transducer 100, with elements as described above with reference to FIG. 1. Connected to at least one signal electrode 140 are the circuit components that will be described hereinafter, which allow for the capacitive micro-fabricated electrostatic transducer 100 to transmit and receive signals. The capacitive micro-fabricated electrostatic transducer circuit 200 also includes a switched balancing reactance 224, which, as described hereinafter, will allow for the balancing of the negative reactance of the capacitive element of the capacitive micro-fabricated electrostatic transducer 100 during a transmit mode.

The transmit circuitry 220 of the capacitive micro-fabricated electrostatic transducer circuit 200 includes a signal generator 222 that generates a transmit frequency drive voltage as appropriate for the application, and is selected in combination with the geometry of the various elements of the capacitive micro-fabricated electrostatic transducer 100. This drive voltage is preferably as small as possible, since that allows for many efficiencies to be gained both in terms of the signal generator 222 used, and the tolerance of the design of the capacitive micro-fabricated electrostatic transducer 100. The balancing reactance 224 is connected between the signal generator and a switching block 226. The balancing reactance 224 is chosen to have a value that counteracts the negative reactance of the capacitive electrostatic transducer 100 at a desired operating frequency. While the balancing reactance 224 is typically implemented as a series inductor, as is illustrated in FIG. 2A, it is noted that the balancing reactance 224 can also be implemented as parallel components, such as parallel inductors, a combination of either series or parallel components, or a combination of series and parallel components. It is also noted that if an electrical transformer is used in the transmit path, it will provide some inductance that may form all or part of the total inductance required for tuning out the negative reactance of the capacitive micro-fabricated electrostatic transducer 100.

Figure 2B:
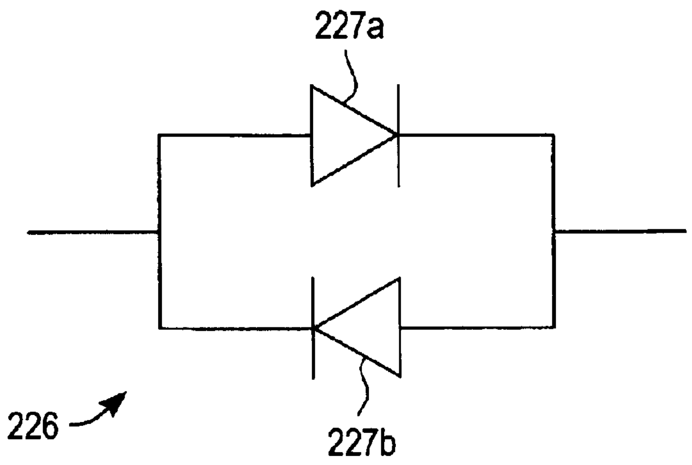
Figure 2C:
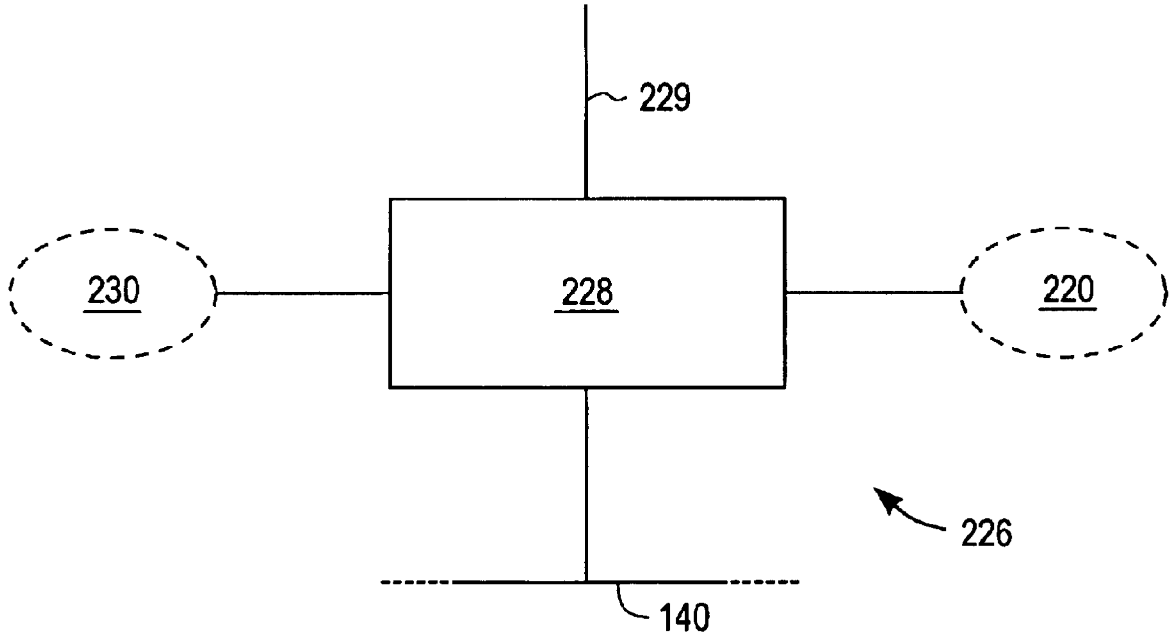

The switching block 226 is chosen so as to allow sufficiently fast switching between the transmit mode, during which the acoustic signal is generated by the capacitive electrostatic transducer 100, and the receive mode, during which reflected acoustic signals are detected by the capacitive electrostatic transducer 100. The switching block 226 can use diodes (illustrated in FIG. 2B), a multiplexer (see FIG. 2C), or other switching means. Generally the switching block 226 is solid state but can in principle be mechanical—including micro-machined mechanical switches. Depending on the configuration of the balancing reactance 224 the switching block 226 may operate in either a closed or open mode during transmit and the opposite mode (i.e. open or closed, respectively) during receive. In a more complex circuit involving a combination of parallel and series balancing components there may be more than one switching block and these switching blocks may operate in different switching modes (i.e. one may close after transmit and another may open after transmit). What is important is that the effect of the reactive balancing component(s) should be included in the circuit during transmit and isolated (or partially isolated) during receive. If diodes **227*a* & 227*b* are used as illustrated in FIG. 2B, opposite terminals of each diode can be connected together to form the switching block 226, such that each is in a forward bias state during one of the positive or negative portions of the transmit signal, and the existence of the diodes 227*a* & 227*b* isolates the impedance of the balancing reactance 224 from both the receive circuit 230 and the capacitive electrostatic transducer 100. If needed, the transmit circuit 220 can include provisions to compensate for any voltage drop across the switching block 226, such as the forward-bias voltage drop across a diode (typically about 0.7V) to each positive and negative portions of the signal waveform generated by the signal generator 222. Alternatively, if the switching block 226 is implemented as a multiplexer 228, as illustrated in FIG. 2C, a control line 229 is additionally needed to transmit a control signal that will cause switching between transmit circuitry 220 and receive circuitry 230**, as shown.

The receive circuitry 230 includes a preamplifier 232 that initially amplifies signals received by the capacitive electrostatic transducer 100. The receive circuitry can also include filters, such as the filters 234 & 236 that are shown. The filters 234 & 236 provide filtering in the vicinity of the second harmonic of the transmitted frequency, where the transmitted frequency is related to the series resonant frequency of the capacitive electrostatic transducer 100 and the balancing reactance 224. For a further discussion of other considerations that are relevant to the overall operation of the receive circuit 230, but not the present invention as described herein, see the article entitled "Surface Micromachined Capacitive Ultrasonic Transducers" by Ladabaum et al, in IEEE Trans. EFFC Vol. 45, No. 3, May 1998.

The transmit circuitry 220 and the receive circuitry 230 can be formed as either part of the same semiconductor substrate 110 that is used to form the capacitive electrostatic transducer 100 or as a circuit that is separate from it. Preferably, however, at least the preamplifier 232 of the receive circuitry 230 is formed on the same semiconductor substrate 110 that is used to form the capacitive electrostatic transducer 100, as well as the balancing reactance 224. In particular, the balancing reactance 224, when used with a micromachined transducer, is implemented as a microinductor using, for example, techniques that have been described by Allen et al. at Georgia Tech. University in, "Micromachined Inductors with Electroplated Magnetically Anisotropic Alloy Cores" in Proceedings of the Fifth International Symposium on Magnetic Materials, Processes, and Device Applications to Storage and Microelectromechanical Systems (MEMS); Electrochem. Soc. 1999, pp 389–401 and "New Micromachined Inductors on Silicon Substrates," in EEE Transactions on Magnetics, vol. 35. no. 5 pt 2. September 1999, p 3547–49. Accordingly, these components can be formed using conventional fabrication techniques, and a further description of their formation is not believed necessary.

During transmission of the preferred embodiment shown in FIG. 2, the receive circuitry 230 is left connected to the capacitive micro-fabricated electrostatic transducer circuit 200. Whereas during reception, the transmit circuitry 220 is effectively disconnected from the transducer circuit 200 by switching block 226, and thus, the receive circuitry 230 is left untouched by the effects of the balancing reactance 224 in the transmit circuitry 220.

The basic operation of the presently preferred embodiment of the present invention shown in FIG. 2A includes applying a DC bias voltage 210 to the capacitive electrostatic transducer 100. Initially, an acoustic signal is generated by generating a signal from the signal generator 222, which signal is tuned as a result of the balancing reactance 224 and drives the capacitive electro-static transducer 100, thereby creating the acoustic signal that emanates therefrom at a frequency corresponding to the frequency of the transmit signal.

During a transmit mode, the capacitance of the capacitive electro-static transducer 100 produces a negative reactance component that is counteracted by the positive reactance of the balancing reactance 224, which is selected for that purpose. The balancing reactance 224 should be selected to withstand the voltages and currents to which it is expected to be subjected.

When the capacitive electro-static transducer 100 is in a receive mode and a reflected signal is thereafter received, the separation 150 as a function of time between the upper conductive plate 160 and the lower conductive plate 170 changes according to the received acoustic pressure function. This change in plate separation 150 causes a change in capacitance and this change in capacitance can be detected in one of several ways. For example, an AC voltage can be applied from a fixed AC source via a resistor. As the capacitance changes as a function of the received acoustic pressure, the capacitor impedance changes and hence the potential detected across the capacitor changes. Other more sophisticated approaches to measuring capacitance change exist. As one example, the method described by Ergun et al. in 'A New Detection Method for Capacitive Micromachined Ultrasonic Transducers' (EEE Trans. UFFC Vol. 48, No.4, pp. 932–942) may be suitable. The balancing reactance 224 is in the transducer circuit 200 only during the transmit pulse duration. In the case of a 2 MHz transducer, this transmit pulse may last on the order of 0.25 to 2.0 microseconds. The switching block 226 that isolates the balancing reactance 224 operates at some small interval after the end of the transmit pulse excitation. This switching block 226 operation may occur, for example, between 0.0 and 2.0 microseconds after the end of the transmit pulse. The switching block 226 may operate before the transducer has completely stopped vibrating as a result of the transmit excitation. However, the switching block 226 should operate before the first meaningful reflected signals are received. It is well known that the first instant after the transmit pulse, the transducer is subjected to 'main bang' effects that may saturate the receive circuitry 230. The timing of the switching block 226 operation and timing of a switch (if one is present) that switches in the receive circuitry 230 (which is normally 'protected' from the transmit waveform) may be subject to experimental or theoretical optimization in terms of useful received reflected signal. Hence, the average capacitance, C, of the capacitive electro-static transducer 100 is changed, as is apparent from the well-known formula $C=((\epsilon*A)/D)$, where $\epsilon$=dielectric constant of insulation between plates, A=area of plates, and D=plate separation. This formula gives the average capacitance as the membrane is at rest. The capacitance will change slightly during vibration but the above calculation is sufficient for designing the preferred transducer circuit 200. Specifically, during transmit mode, the charge, Q, on the capacitive electro-static transducer 100 is a function of the drive voltage obtained from the signal generator 222. During the receive mode, the acoustic signals received will cause a different vibration of the membrane 130, and, therefore, a change in capacitance from that which existed during the transmit mode. This changed capacitance is thus detected as the receive signal generated from the capacitive electro-static transducer 100, which receive signal is supplied via at least one signal electrode 140 to the preamplifier 232. It is noted that there are stray capacitance issues associated with the received signal that are known, and, as a result, they are not discussed further herein.

Figure 3:
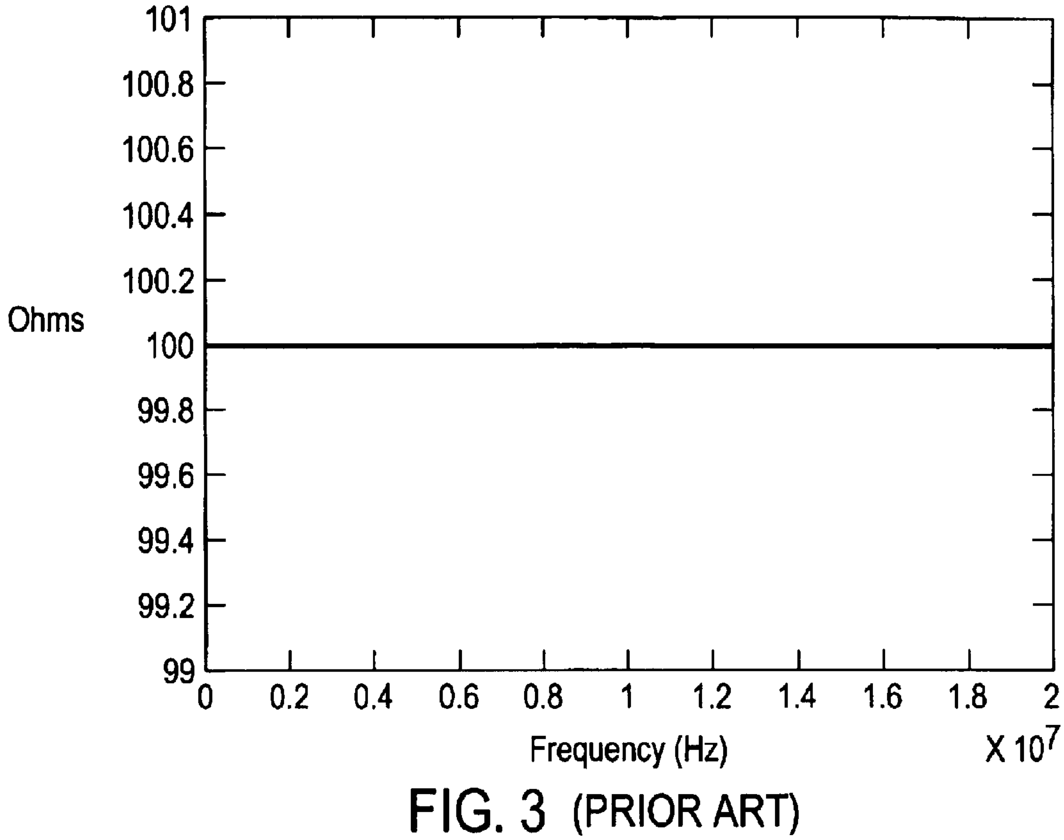
FIG. 3 (PRIOR ART)
FIG. 3 illustrates the real part of the impedance of a capacitive electrostatic transducer.
Figure 4:
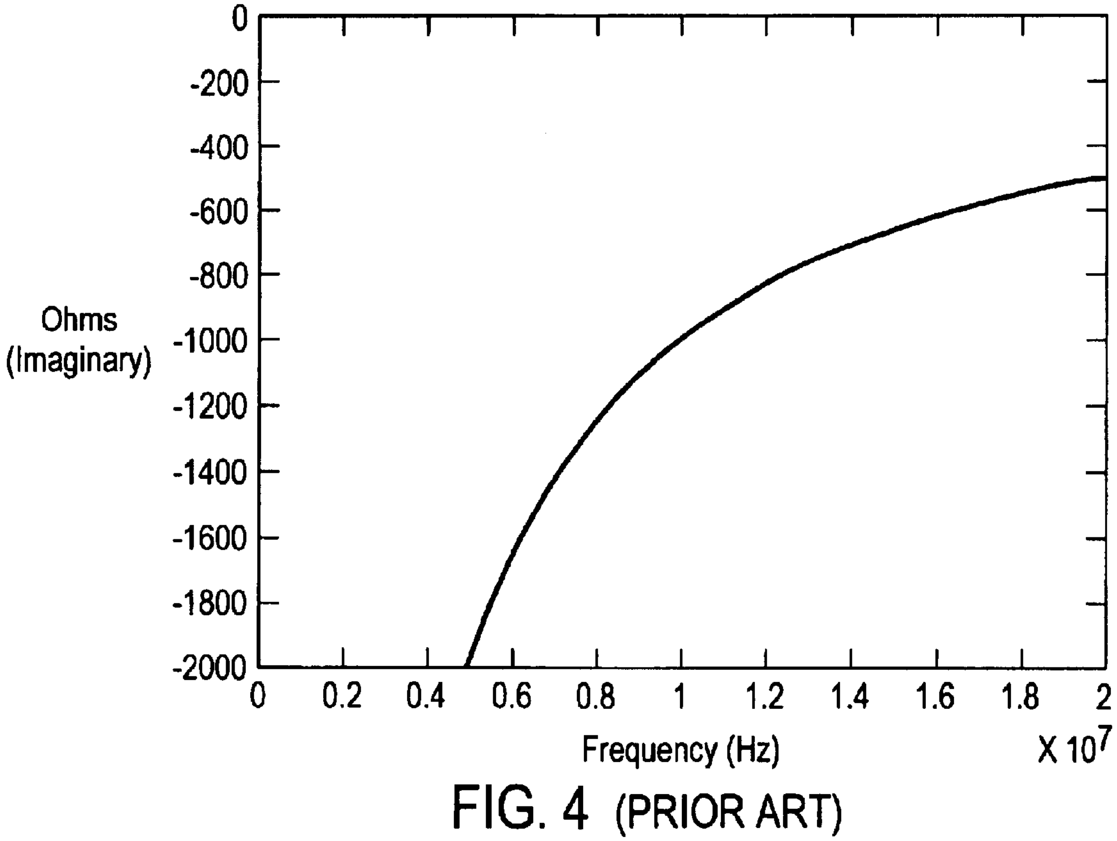
FIG. 4 (PRIOR ART)
FIG. 4 illustrates the imaginary part of the impedance of a capacitive electrostatic transducer.
Figure 5:
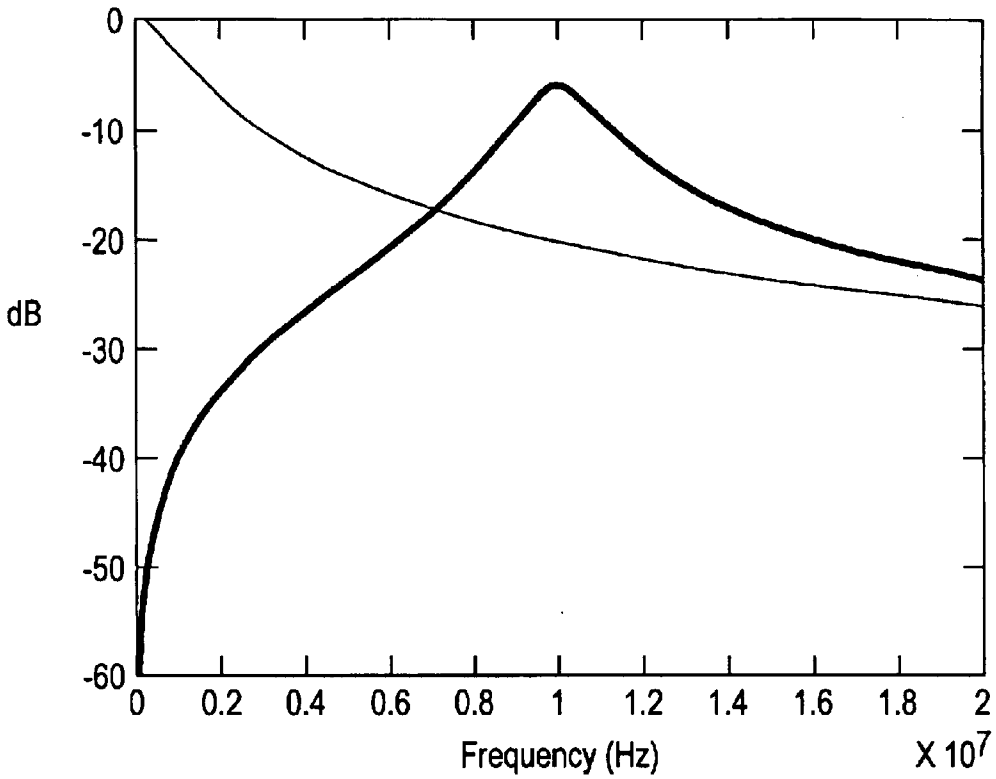
FIG. 5 illustrates a comparison of the voltage delivered to the real part of the transducer impedance with and without series inductance tuning.

To illustrate the reactance selection for this preferred embodiment of the present invention, assume, as is well known, that the typical impedance of an immersion (water use) electro-acoustic transducer is between 50 and 100 ohms. FIG. 3 illustrates an assumed real component of the capacitive electro-static transducer 100 impedance of 100 ohms. Capacitance at this impedance corresponds to approximately 15 pF, which is also approximately typical and well known in the art. FIG. 4 indicates that the series imaginary impedance for a capacitance of 15 pF is approximately −1000 ohms at a desired operating frequency of 10 MHz. Thus, without the balancing reactance of the preferred embodiment of the present invention, the current available to the real part of the transducer impedance (which is responsible for energy conversion) is approximately 10% of its maximum. Therefore, as shown in FIG. 2A, the preferred embodiment of the present invention inserts a balancing reactance 224, illustrated as a series inductor, with an impedance of +1000 imaginary ohms at 10 MHz to counteract the negative reactance of the capacitive electrostatic transducer 100 at a desired 10 MHz operating frequency. Under these exemplary conditions, this equates to inserting a 16 $\mu$H series inductor. FIG. 5 illustrates the resulting improvement on the voltage delivered to the real part of the transducer impedance because of the presently preferred embodiment of the present invention. At the exemplary desired operating frequency of 10 MHz, the delivered voltage is improved by more than 10 dB.

Figure 6:
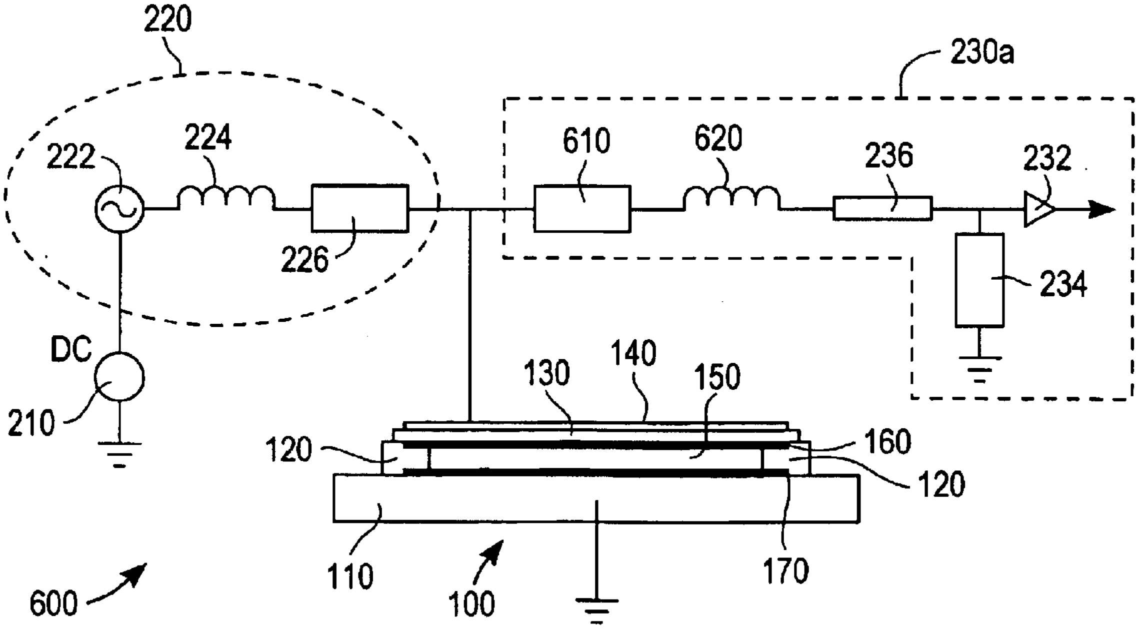
FIG. 6 illustrates a micro-fabricated capacitive electrostatic transducer with a switched balancing reactance according to another embodiment of the present invention.

Another embodiment of the present invention is shown in FIG. 6, and illustrates the further inclusion of a receive balancing reactance 620, also preferably implemented using a series inductor, and a receive switching block 610 inserted in the receive circuit 230*a* closest to the capacitive electrostatic transducer 100, with the other components of this alternate capacitive, micro-fabricated electrostatic transducer circuit 600 the same as the circuit 200 illustrated in FIG. 2A. This alternate circuit 600 would typically still include a balancing reactance 224 in the transmit circuit 220, which would still be selected to tune out the negative reactance of the capacitive electrostatic transducer during transmission.

The value of the receive balancing reactance 620 of this embodiment has a different value from the balancing reactance 224 of the transmit circuit 220, as described hereinafter, but would also be isolated from the transmit circuit 220 by the receive switching block 610, as illustrated, during a receive mode. The receive switching block 610 would be open during transmit (isolating the receive balancing reactance 620 from the transmit circuit 220) and closed during receive, so as to switch in the receive balancing reactance 620 during receive. The switching block 226 would operate as previously discussed and in an opposite mode to receive switching block 610—i.e. the switching block 226 would be closed during transmit so as to include the balancing reactance 224 but open during receive to isolate the balancing reactance 224 from the receive circuitry 230*a*. The receive switching block 610 can be made of the same types of components as is the switching block 226 previously described, such as with reference to FIGS. 2B and 2C.

As an example of selecting the receive balancing reactance 620, assume the same conditions provided in the previous example above, except assume the desired operating frequency is 20 MHz—the 'second' harmonic of the 10 MHz transmit center frequency ('first' harmonic or 'fundamental'). With an electrostatic transducer capacitance of 15 pF, the receive circuit 230*a* receive balancing reactance 620 of this embodiment would preferably be 4.2 $\mu$H. As with the preferred embodiment discussed above, the receive balancing reactance 620 can also be implemented as a series component, a parallel component, a combination of series or parallel components, or a combination of series and parallel components.

While the present invention has been described herein with reference to particular embodiments thereof, a latitude of modification, various changes and substitutions are intended in the foregoing disclosure. Accordingly, it will be appreciated that in some instances some features of the invention will be employed without a corresponding use of other features without departing from the spirit and scope of the invention as set forth in the appended claims.

What is claimed is:

1. A method for tuning an electro-acoustic transducer circuit comprising:

identifying an electro-acoustic transducer circuit including a transmit signal path, a receive signal path and a capacitive electrostatic transducer, the capacitive electrostatic transducer having a negative reactive characteristic and an operating center frequency, wherein the transmit signal path and the receive signal path are electrically coupled to the capacitive electrostatic transducer;

inserting a balancing reactance into the transmit signal path to assist in countering the negative reactive characteristic at the operating center frequency during a transmit mode of the electro-acoustic transducer circuit; and isolating the balancing reactance from the receive signal path and the capacitive electrostatic transducer during a receive mode of the electro-acoustic transducer circuit.

2. The method of claim 1, wherein the capacitive electrostatic transducer is micro-fabricated.

3. The method of claim 1, wherein the balancing reactance is inductance.

4. The method of claim 3, wherein the inductance is series inductance.

5. The method of claim 3, wherein the inductance is parallel inductance.

6. The method of claim 3, wherein the inductance is a combination of series inductance and parallel inductance.

7. The method of claim 3, wherein the inductance is selected to cancel the negative reactive characteristic of the electro-acoustic capacitive transducer at the operating center frequency, thereby resulting in a resonant circuit with a resonant frequency at the operating center frequency.

8. The method of claim 1, wherein the step of isolating the balancing reactance during the receive mode is achieved using a switch that isolates the transmit signal path from both the receive signal path and the electro-acoustic capacitive transducer.

9. The method of claim 8, wherein the switch uses a pair of diodes.

10. The method of claim 8, wherein the switch uses at least one multiplexer.

11. The method of claim 1, further comprising the step of filtering a receive signal during the receive mode to substantially pass a second harmonic of a transmit signal.

12. The method of claim 11, wherein the second harmonic of the transmit signal includes as elements thereof a resonant frequency of the transmit signal and the balancing reactance added by the step of inserting.

13. The method of claim 11, wherein the capacitive electrostatic transducer is micro-fabricated.

14. The method of claim 11, where in the balancing reactance is inductance.

15. The method of claim 11, wherein the step of isolating the balancing reactance during the receive mode is achieved using a switch that isolates the transmit signal path from both the receive signal path and the electro-acoustic capacitive transducer.

16. The method of claim 1, wherein the capacitive electrostatic transducer includes at least one electrode, the at least one electrode being electrically coupled to the transmit signal path and the receive signal path.

17. The method of claim 16, wherein the capacitive electrostatic transducer is micro-fabricated.

18. The method of claim 16, wherein the balancing reactance is inductance.

19. The method of claim 18, wherein the inductance is selected to cancel the negative reactive characteristic of the electro-acoustic capacitive transducer at the operating center frequency, thereby resulting in a resonant circuit with a resonant frequency at the operating center frequency.

20. The method of claim 16, wherein the step of isolating the balancing reactance during the receive mode is achieved using a switch that isolates the transmit signal path from both the receive signal path and the electro-acoustic capacitive transducer.

21. The method of claim 16, further comprising the step of filtering a receive signal during the receive mode to substantially pass a second harmonic of a transmit signal.

22. The method of claim 21, wherein the capacitive electrostatic transducer is micro-fabricated.

23. The method of claim 21, wherein the step of isolating the balancing reactance is achieved using a switch that isolates the receive signal path from the transmit signal path and the electro-acoustic capacitive transducer during the receive mode.

24. A tuned electro-acoustic transducer circuit comprising:

an electro-acoustic transducer circuit including a transmit signal path, a receive signal path and a capacitive electrostatic transducer, the capacitive electrostatic transducer having a negative reactive characteristic and an operating center frequency, wherein the transmit signal path and the receive signal path are electrically coupled to the capacitive electrostatic transducer;

a balancing reactance inserted into the transmit signal path to assist in countering the negative reactive characteristic at the operating center frequency during a transmit mode of the electro-acoustic transducer circuit; and the balancing reactance isolated from the receive signal path and the capacitive electrostatic transducer during a receive mode of the electro-acoustic transducer circuit.

25. The circuit of claim 24, wherein the capacitive electrostatic transducer is micro-fabricated.

26. The circuit of claim 24, wherein the balancing reactance is inductance.

27. The circuit of claim 26, wherein the inductance is series inductance.

28. The circuit of claim 26, wherein the inductance is parallel inductance.

29. The circuit of claim 26, wherein the inductance is a combination of series inductance and parallel inductance.

30. The circuit of claim 26, wherein the inductance is selected to cancel the negative reactive characteristic of the electro-acoustic capacitive transducer at the operating center frequency, thereby resulting in a resonant circuit with a resonant frequency at the operating center frequency.

31. The circuit of claim 24, wherein the balancing reactance is isolated during the receive mode using a switch that isolates the transmit signal path from both the receive signal path and the electro-acoustic capacitive transducer.

32. The circuit of claim 31, wherein the switch uses a pair of diodes.

33. The circuit of claim 31, wherein the switch uses at least one multiplexer.

34. The circuit of claim 24, further comprising a receive signal filtered during the receive mode to substantially pass a second harmonic of a transmit signal.

35. The circuit of claim 34, wherein the second harmonic of the transmit signal includes as elements thereof a resonant frequency of the transmit signal and the balancing reactance added by the step of inserting.

36. The circuit of claim 34, wherein the capacitive electrostatic transducer is micro-fabricated.

37. The circuit of claim 34, wherein the balancing reactance is inductance.

38. The circuit of claim 34, wherein the balancing reactance is isolated during the receive mode using a switch that isolates the transmit signal path from both the receive signal path and the electro-acoustic capacitive transducer.

39. The circuit of claim 24, wherein the capacitive electrostatic transducer includes at least one electrode, the at least one electrode being electrically coupled to the transmit signal path and the receive signal path.

40. The circuit of claim 39, wherein the capacitive electrostatic transducer is micro-fabricated.

41. The circuit of claim 39, wherein the balancing reactance is inductance.

42. The circuit of claim 41, wherein the inductance is selected to cancel the negative reactive characteristic of the electro-acoustic capacitive transducer at the operating center frequency, thereby resulting in a resonant circuit with a resonant frequency at the operating center frequency.

43. The circuit of claim 39, wherein the balancing reactance is isolated during the receive mode using a switch that isolates the transmit signal path from both the receive signal path and the electro-acoustic capacitive transducer.

44. The circuit of claim 39, further comprising a receive signal filtered during the receive mode to substantially pass a second harmonic of a transmit signal.

45. The circuit of claim 44, wherein the capacitive electrostatic transducer is micro-fabricated.

46. The circuit of claim 44, wherein the balancing reactance is isolated during the receive mode using a switch that isolates the transmit signal path from both the receive signal path and the electro-acoustic capacitive transducer.

* * * * *